United States Patent
Goode, Jr.

(10) Patent No.: US 8,340,747 B2
(45) Date of Patent: *Dec. 25, 2012

(54) METHOD AND APPARATUS FOR TRENDING A PHYSIOLOGICAL CARDIAC PARAMETER

(75) Inventor: Paul V. Goode, Jr., St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/887,273

(22) Filed: Sep. 21, 2010

(65) Prior Publication Data

US 2011/0009767 A1   Jan. 13, 2011

Related U.S. Application Data

(63) Continuation of application No. 11/470,926, filed on Sep. 7, 2006, now Pat. No. 7,826,891, which is a continuation of application No. 10/603,876, filed on Jun. 25, 2003, now Pat. No. 7,171,258.

(51) Int. Cl.
*A61B 5/053* (2006.01)
(52) U.S. Cl. .......................... 600/509; 607/17
(58) Field of Classification Search .................. 600/509; 607/17, 27, 122
See application file for complete search history.

(56) References Cited

U.S. PATENT DOCUMENTS

| | | | |
|---|---|---|---|
| 4,202,340 A | 5/1980 | Langer et al. | |
| 4,674,518 A | 6/1987 | Salo | |
| 4,733,667 A | 3/1988 | Olive et al. | |
| 4,809,697 A * | 3/1989 | Causey et al. | 607/31 |
| 5,058,583 A | 10/1991 | Geddes et al. | |
| 5,113,869 A | 5/1992 | Nappholz et al. | |
| 5,154,171 A * | 10/1992 | Chirife | 607/24 |
| 5,178,151 A | 1/1993 | Sackner | |
| 5,190,035 A | 3/1993 | Salo et al. | |
| 5,300,093 A | 4/1994 | Koestner et al. | |
| 6,021,350 A | 2/2000 | Mathson | |
| 6,058,328 A * | 5/2000 | Levine et al. | 607/14 |
| 6,134,469 A | 10/2000 | Wietholt | |
| 6,278,894 B1 | 8/2001 | Salo et al. | |

(Continued)

FOREIGN PATENT DOCUMENTS

EP   0985429 A2   3/2000

OTHER PUBLICATIONS

"U.S. Appl. No. 10/603,876, Prosecution File History", 59 pgs, Complete as of Oct. 27, 2007.

(Continued)

*Primary Examiner* — Rex R Holmes
(74) *Attorney, Agent, or Firm* — Schwegman Lundberg & Woessner, P.A.

(57) ABSTRACT

The present invention relates to an implantable cardioverter-defibrillator or pacemaker whose standard circuitry is used to trend a physiological cardiac parameter using intra-cardiac impedance measurements. The trend information may be used to predict the onset of a sudden cardiac death (SCD) event. By being able to predict the onset of an SCD event, patients and their physicians may be forewarned of a life-threatening event allowing them to respond accordingly. The trend information may also be used to predict the efficacy of cardiac-related medications, monitor progress of congestive heart failure, detect the occurrence of myocardial infarction, or simply track changes in sympathetic tone.

17 Claims, 7 Drawing Sheets

U.S. PATENT DOCUMENTS

| | | | |
|---|---|---|---|
| 6,473,640 B1 | 10/2002 | Erlebacher | |
| 6,589,188 B1 | 7/2003 | Street et al. | |
| 6,604,000 B2 | 8/2003 | Lu | |
| 6,708,061 B2* | 3/2004 | Salo et al. | 607/9 |
| 6,738,667 B2* | 5/2004 | Deno et al. | 607/23 |
| 7,171,258 B2 | 1/2007 | Goode | |
| 7,190,996 B2 | 3/2007 | Jarverud | |
| 7,215,997 B2 | 5/2007 | Yu et al. | |
| 7,539,533 B2 | 5/2009 | Tran | |
| 7,577,478 B1 | 8/2009 | Kroll et al. | |
| 2001/0003160 A1 | 6/2001 | Meyer | |
| 2003/0120164 A1* | 6/2003 | Nielsen et al. | 600/513 |
| 2005/0043675 A1 | 2/2005 | Pastore et al. | |
| 2005/0288721 A1 | 12/2005 | Girouard et al. | |
| 2006/0259087 A1 | 11/2006 | Baynham et al. | |
| 2006/0287684 A1 | 12/2006 | Baynham et al. | |
| 2007/0043393 A1 | 2/2007 | Brockway et al. | |
| 2007/0049835 A1 | 3/2007 | Goode | |
| 2007/0054871 A1 | 3/2007 | Pastore et al. | |
| 2007/0150005 A1 | 6/2007 | Sih et al. | |
| 2007/0150015 A1 | 6/2007 | Zhang et al. | |
| 2007/0162081 A1 | 7/2007 | Yu et al. | |
| 2007/0276453 A1 | 11/2007 | Hill et al. | |
| 2007/0299356 A1 | 12/2007 | Wariar et al. | |
| 2008/0081354 A1 | 4/2008 | Qu et al. | |
| 2008/0091138 A1 | 4/2008 | Pastore et al. | |
| 2008/0177194 A1 | 7/2008 | Zhang et al. | |

OTHER PUBLICATIONS

"U.S. Appl. No. 11/470,926, Response filed Jan. 20, 2009 to Non Final Office Action mailed Sep. 17, 2008", 9 pgs.

"U.S. Appl. No. 11/470,926, Supplemental Notice of Allowability Mailed Jul. 21, 2010", 2 pgs.

"U.S. Appl. No. 11/470,926, Non-Final Office Action mailed Sep. 17, 2008", 7 pgs.

"U.S. Appl. No. 11/470,926, Final Office Action mailed May 7, 2009", 8 pgs.

"U.S. Appl. No. 11/470,926, Notice of Allowance mailed Jun. 28, 2010", 7 pgs.

"U.S. Appl. No. 11/470,926, Response filed Jul. 7, 2009 to Final Office Action mailed May 7, 2009", 9 pgs.

"U.S. Appl. No. 11/470,926, Response filed Mar. 4, 2010 to Non Final Office Action mailed Feb. 5, 2010", 9 pgs.

"U.S. Appl. No. 11/470,926, Non-Final Office Action mailed Feb. 5, 2010", 8 pgs.

"International Application No. PCT/US2004/020307, International Search Report mailed Nov. 18, 2004", 5 pgs.

"International Application No. PCT/US2004/020307, Written Opinion mailed Nov. 18, 2004", 7 pgs.

Cao, et al., "Nerve Sprouting and Sudden Cardiac Death", Circulation Research,, (04 14 00), 816-821.

Cao, et al., "Relationship Between Regional Cardiac Hyperinnervation and Ventricular Arrhythmia", Circulation, (04 25 00), 1960-1969.

Geddes, L., et al., "Continuous Measurement of Ventricular Stroke Volume by Electrical Impedance", Cardiovascular Research Center Bulletin, vol. 4, No. 4, (Apr. 1, 1966), 118-131.

Grubb, et al., "Pacing and Clinical Electrophysiology, Adaptive Rate Pacing Controlled by Right Ventricular Preejection Interval for Severe Refractory Orthostatic Hypotension", (1993), 801-805.

Lown, et al., "Neural Activity and Ventricular Fibrillation", The New England Journal of Medicine, (1976), 1165-1170.

Lown, et al., "Sleep and Ventricular Premature Beats", Circulation, (1973), 691-701.

McGoon, et al., "The Feasibility of Utilizing the Systolic Preejection Interval as a Determinant of Pacing Rate", Journal of the American College of Cardiology, (1989), 1753-1758.

Salo, Rodney W., "Continuous ventricular volume assessment for diagnosis and pacemaker control", Pacing Clin Electrophysiol., 7(6 Pt 2), (Nov. 1984), 1267-1272.

Schaldach, M., "Automatic adjustment of pacing parameters based on intracardiac impedance measurements", Pacing Clin Electrophysiol., 13(12 Pt 2), (Dec. 1990), 1702-1710.

Schaldach, M., "Electrotherapy of the Heart: Technical Aspects of Cardiac Pacing", Springer-Verlag Berlin Heidelberg, (1992), 132 pgs.

Schwartz, et al., "Autonomic Nervous System and Sudden Cardiac Death", Supplement to Circulation, (1992), I-77 to I-91.

Zipes, et al., "Influence of the Autonomic Nervous System on the Genesis of Cardiac Arrhythmias", Pacing and Clinical Electrophysiology, (1983), 1210-1220.

\* cited by examiner

METHOD AND APPARATUS FOR TRENDING A PHYSIOLOGICAL CARDIAC PARAMETER

CROSS-REFERENCE TO RELATED APPLICATIONS

This application is a continuation of U.S. application Ser. No. 11/470,926, filed on Sep. 7, 2006, now issued as U.S. Pat. No. 7,826,891, which is a continuation of U.S. application Ser. No. 10/603,876, filed on Jun. 25, 2003, now issued as U.S. Pat. No. 7,171,258, which are incorporated herein by reference, and the benefit of priority of each of which are claimed hereby.

FIELD OF INVENTION

The present system relates generally to implantable cardioverter-defibrillators and pacemakers and particularly, but not by way of limitation, to such systems being used to trend a physiological parameter using intra-cardiac impedance measurements.

BACKGROUND OF THE INVENTION

The heart is generally divided into four chambers, the left and right ventricles and the left and right atria. Blood passes from the right atrium into the right ventricle via the tricuspid valve. The atrial chambers and the ventricular chambers undergo a cardiac cycle consisting of one complete sequence of contraction and relaxation of the chambers of the heart. The term systole describes the contraction phase of the cardiac cycle during which the ventricular muscle cells contract to pump blood through the circulatory system. The term diastole describes the relaxation phase during which the ventricular muscle cells relax, causing blood from the atrial chamber to fill the ventricular chamber. After completion of the period of diastolic filling, the systolic phase of a new cardiac cycle is initiated.

Through the cardiac cycle, the heart is able to pump blood throughout the circulatory system. Effective pumping of the heart depends upon five basic requirements. First, the contractions of cardiac muscle must occur at regular intervals and be synchronized. Second, the valves separating the chambers of the heart must fully open as blood passes through the chambers. Third, the valves must not leak. Fourth, the contraction of the cardiac muscle must be forceful. Fifth, the ventricles must fill adequately during diastole.

When functioning properly, the human heart maintains its own intrinsic rhythm based on physiologically-generated electrical impulses. However, when contractions of the heart are not occurring at regular intervals, or are unsynchronized, the heart is said to be arrhythmic. During an arrhythmia, the heart's ability to effectively and efficiently pump blood is compromised. Many different types of arrhythmias have been identified. Arrhythmias can occur in either the atria or the ventricles. Arrhythmias may be the result of such conditions as myocardial infarction, cardiomyopathy or carditis.

Ventricular fibrillation is an arrhythmia that occurs in the ventricles of the heart. In ventricular fibrillation, various areas of the ventricle contract asynchronously. During ventricular fibrillation the heart fails to pump blood. If not corrected, the failure to pump blood and thereby maintain the circulation can have fatal consequences.

Ventricular tachycardia is an arrhythmia that occurs in the ventricular chambers of the heart. Ventricular tachycardias are typified by ventricular rates between 120-250 beats per minute and are caused by electrical or mechanical disturbances within the ventricles of the heart. During ventricular tachycardia, the diastolic filling time is reduced and the ventricular contractions are less synchronized and therefore less effective than normal. If not treated quickly, a ventricular tachycardia could develop into a life-threatening ventricular fibrillation.

Supraventricular tachycardias occur in the atria. Examples of these include atrial tachycardias, atrial flutter and atrial fibrillation. During certain supraventricular tachycardias, aberrant cardiac signals from the atria drive the ventricles at a very rapid rate.

Sudden cardiac death (SCD) may be a consequence of cardiac rhythm abnormalities occurring in the ventricles or the atria such as ventricular fibrillation, ventricular tachycardia or one of the supraventricular tachycardias. Sudden cardiac death fatally afflicts about 300,000 Americans each year.

Patients with chronic heart disease can receive implantable cardiac devices such as pacemakers, implantable cardioverter-defibrillators and HF cardiac resynchronization therapy devices. Implantable cardioverter-defibrillators (ICDs) are used as conventional treatment for patients whose arrhythmic conditions cannot be controlled by medication. These devices provide large shocks to the heart in an attempt to revive a patient from a cardiac rhythm abnormality that may result in an SCD occurrence. At the present there are no firm predictors for SCD within these devices.

SUMMARY OF THE INVENTION

This document discusses an implantable cardioverter-defibrillator or pacemaker whose standard circuitry is used to trend a physiological cardiac parameter using intra-cardiac impedance measurements. The trend information may be used to predict the onset of an SCD event. By being able to predict the onset of an SCD event, patients and their physicians may be forewarned of a life-threatening event allowing them to respond accordingly. The trend information may also be used to predict the efficacy of cardiac-related medications, monitor progress of congestive heart failure, detect the occurrence of myocardial infarction, or simply track changes in sympathetic tone.

In one embodiment of the present invention, a method of predicting sudden cardiac death includes the steps of determining intra-cardiac impedance, deriving a physiologic cardiac parameter from the determined impedance, trending the parameter over spaced time intervals, and predicting the onset of a sudden cardiac death episode.

In another embodiment, a system for predicting sudden cardiac death episode includes a device that measures intra-cardiac impedance, a derivation module that derives a physiological cardiac parameter from the measured impedance, and a module that trends the derived parameter over spaced time intervals to create trend data. The system may also include an analyzing module that analyzes the trend data to predict a sudden cardiac death episode.

In a further embodiment, a method of trending a cardiac parameter includes the steps of measuring an intra-cardiac impedance, determining a physiologic parameter using the intra-cardiac impedance, and trending the cardiac parameter over time.

In a yet further embodiment, a device for trending a physiological cardiac parameter includes an impedance module that measures intra-cardiac impedance, a parameter module that calculates cardiac parameter values using the measured impedance, and a trending module that generates trend data using cardiac parameter values.

These and various other features, as well as advantages, which characterize the present invention, will be apparent from a reading of the following detailed description and a review of the drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE PREFERRED EMBODIMENT

Figure 1:
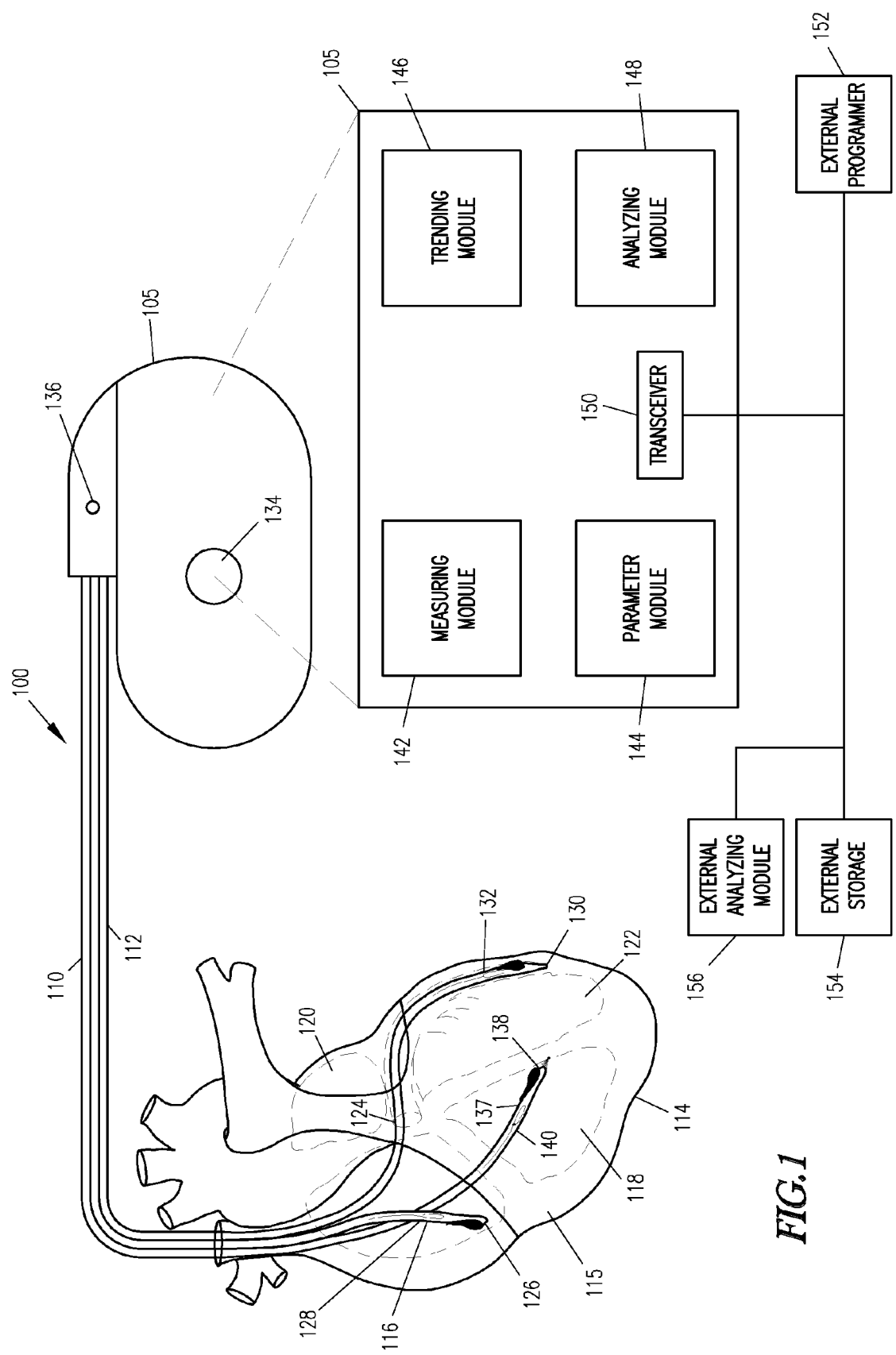
FIG. 1 is a schematic/block diagram illustrating generally, among other things, one embodiment of portions of an impedance sensor for trending a physiological cardiac parameter and an environment in which it is used.

In the following detailed description, reference is made to the accompanying drawings which form a part hereof, and in which is shown by way of illustration specific embodiments or examples. These embodiments may be combined, other embodiments may be utilized, and structural, logical and electrical changes may be made without departing from the spirit and scope of the present invention. The following detailed description is therefore, not to be taken in a limiting sense, and the scope of the present invention is defined by the appended claims and their equivalents.

The present system and methods are described with respect to implantable cardiac rhythm management (CRM) devices, such as pacemakers, cardioverter defibrillators (ICDs), pacer/defibrillators, and multi-chamber and/or multi-site (in a single chamber or multiple chambers) cardiac resynchronization therapy (CRT) devices that utilize standard pacing and defibrillating leads. The software directing operation of such devices may be modified in a way to utilize intra-cardiac impedance measurements collected by the device to generate a physiological cardiac parameter. The device may also be programmed to trend the generated parameter over time. The trend information may represent changes in sympathetic activity of cardiac tissue and thereby be used to track certain physiologic indicators such as, for example, the prediction of a sudden cardiac death (SCD) event, the efficacy of cardiac-related medications being taken by the patient, the detection of a myocardial infarction, or the progress of congestive heart failure in a patient. For example, one trend may show a slow decrease in overall sympathetic activity over time, while another trend may show a sharp drop in sympathetic activity that is sustained for a given period of time, while yet another trend may show spikes of sympathetic activity at certain times during each day that may be related to how the heart is reacting during specific activities. Because certain trends may indicate a specific physiological indicator (as listed above), the system of the present invention may be configured to identify the occurrence of certain physiological indicators from trend information. Such physiologic parameters may be referred to as "predetermined physiological indicators" to the extent that the system may be configured to identify and track one or more specific indicators based on the trend information.

Sympathetic activity refers to the level of activation of the autonomic nervous system, specifically the sympathetic nerves that regulate cardiac muscle contraction. Increased sympathetic activity (or tone) is an important contributor to the generation of spontaneous life-threatening arrhythmias and SCD. Changes in sympathetic activity during specific patient activities (such as exercise or sleep) over time may provide important information for the patient and their physician.

There are several physiological cardiac parameters that may be generated from intra-cardiac impedance measurements that provide insight into sympathetic activity by inferring their effects on cardiac contractility. Three exemplary parameters are stroke volume, ejection fraction, and pre-ejection period (PEP). "Stroke volume" refers to the volume of blood pumped from a ventricle of the heart in one beat. "Ejection fraction" refers to the ratio of the volume of blood the heart empties during systole to the volume of blood in the heart at the end of diastole expressed as a percentage. "Pre-ejection period" measures the latency between the onset of electromechanical systole, and the onset of left-ventricular ejection.

In one example, it is known that PEP shortens when sympathetic activity is increased. This shortened parameter may be measured via intra-cardiac impedance. Therefore, should a patient experience a myocardial infarction (MI), or have already experienced a MI, electrical remodeling will occur in the heart. This remodeling may manifest itself as an increased average sympathetic activity (detected by the shorted PEP values over some time interval), and eventually a life-threatening arrhythmia and possibly even sudden cardiac death.

The following is a detailed description of various systems and methods of generating and trending physiological cardiac parameters based on intra-cardiac impedance that are used to track certain physiological indicators. FIG. 1 is a schematic/block diagram illustrating generally one embodiment of portions of a system 100 of the present invention and an environment in which it is used. In this embodiment, system 100 includes, among other things, an CRM device 105, which is coupled by leads 110, 112, 137 to heart 114. Heart 114 includes four chambers: right atrium 116, right ventricle 118, left atrium 120 and left ventricle 122. Heart 114 also includes a coronary sinus 124, a vessel that extends from right atrium 116 toward the left ventricular free wall, and which, for the purpose of this document, is considered to include the great cardiac vein and/or tributary vessels.

Lead 110 may include an electrode associated with right atrium 116, such as a tip electrode 126 and/or ring electrode 128. The electrode is "associated" with the particular heart chamber by inserting it into that heart chamber, by inserting it into a portion of the heart's vasculature that is close to that heart chamber, by epicardially placing the electrode outside that heart chamber, or by any other techniques of configuring and situating an electrode for sensing signals and/or providing therapy with respect to the heart chamber.

Lead 112, which is introduced into coronary sinus 124 and/or the great cardiac vein or one of its tributaries, includes one or a plurality of electrodes associated with left ventricle 122, such as tip electrode 130 and/or ring electrode 132. Lead 137 includes one or a plurality of electrodes associated with the right ventricle, such as tip electrode 138 and/or ring electrode 140.

Device 105 may also include other electrodes, such as housing electrode 134 and/or header electrode 136, which are useful for, among other things, unipolar sensing of heart signals or unipolar delivery of contraction-evoking stimulations in conjunction with one or more of the electrodes 126, 128, 130, 132, 138, 140 associated with heart 115. Electrodes 134 and 136 may be referred to in the art as "can" electrodes, such that electrodes 126, 128, 130, 132, 138, 140 positioned in the heart may be compared to or communicate with the "can" electrodes. Alternatively, bipolar sensing and/or therapy may be used between electrodes 126 and 128, between electrodes 130 and 132, between electrodes 138 and 140, or between any one of the electrodes 126, 128, 130, 132, 138, 140 and another closely situated electrode. In practice, any combination of unipolar and bipolar electrodes positioned within the heart may be used, in addition to combining the electrodes positioned within the heart with "can" electrodes to obtain the necessary impedance measures.

Device 105 may include several features that may be represented by modules, process steps and components as hereinafter described. For example, device 105 may include a measuring module 142 that is coupled to one or more of the electrodes 126-136 for sensing electrical depolarizations and intra-cardiac impedance corresponding with heart chamber contractions. Device 105 may also include a parameter module 144, a trending module 146, an analyzing module 148, and other modules or features relevant to tracking intra-cardiac impedance and trending derived physiologic parameters over time. For example, device 105 may include a transceiver 150 for communication between device 105 and an outside source such as, for example, an external programmer 152, an external storage device 154, or an external analyzing module 156.

Figure 2:
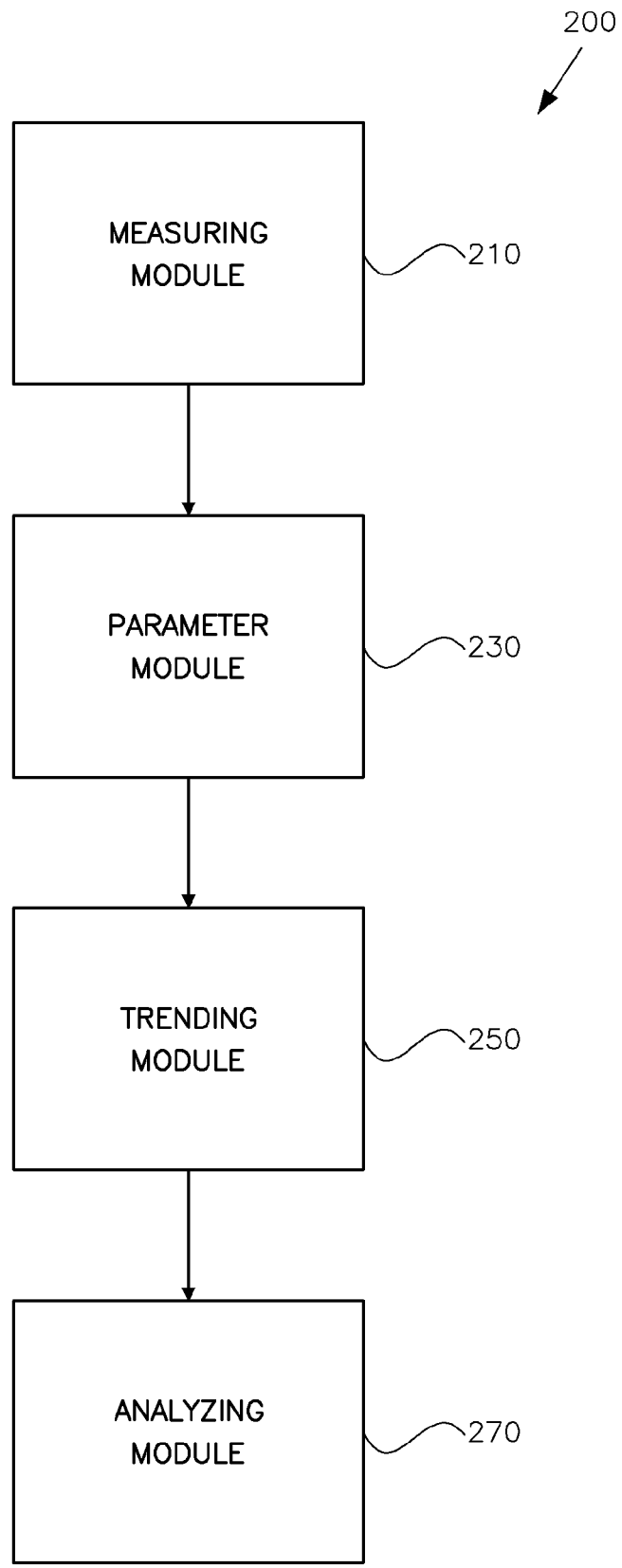
FIG. 2 is a schematic/block diagram illustrating generally, among other things, one embodiment of portions of an impedance sensor for trending a physiological cardiac parameter.

Referring now to FIG. 2, one embodiment of an example system or device 200 for trending a physiological cardiac parameter is provided. System 200 may include a measuring module 210, a parameter module 230, a trending module 250, and in some cases may further include an analyzing module 270. Modules 210, 230, 250 and 270 are further described herein with reference to FIGS. 3-6. In essence, the measuring module 210 is capable of measuring intra-cardiac impedance values in a patient, the parameter module 230 is capable of calculating or otherwise deriving a physiologic cardiac parameter using the measured impedance values, the trending module 250 is capable of generating trend data using the derived parameter values, and the analyzing module 270 is capable of analyzing trend data to track predetermined physiological indicators. In some embodiments, analyzing module 270 is part of a device including measuring, trending and parameter modules, such as the device 105 shown in FIG. 1. In other embodiments, analyzing module 270 may be an external analyzing module, such as module 156 illustrated in FIG. 1, that analyzes trend data at a separate location from the device in which the measuring, parameter and trending modules are located. Also, in other embodiments, system 200 may include other modules or components such as a transceiver 150, a controller (not shown), a signal generator (not shown), etc. if such components or modules are not integrated into the measuring, parameter, trending and analyzing modules.

Figure 3:
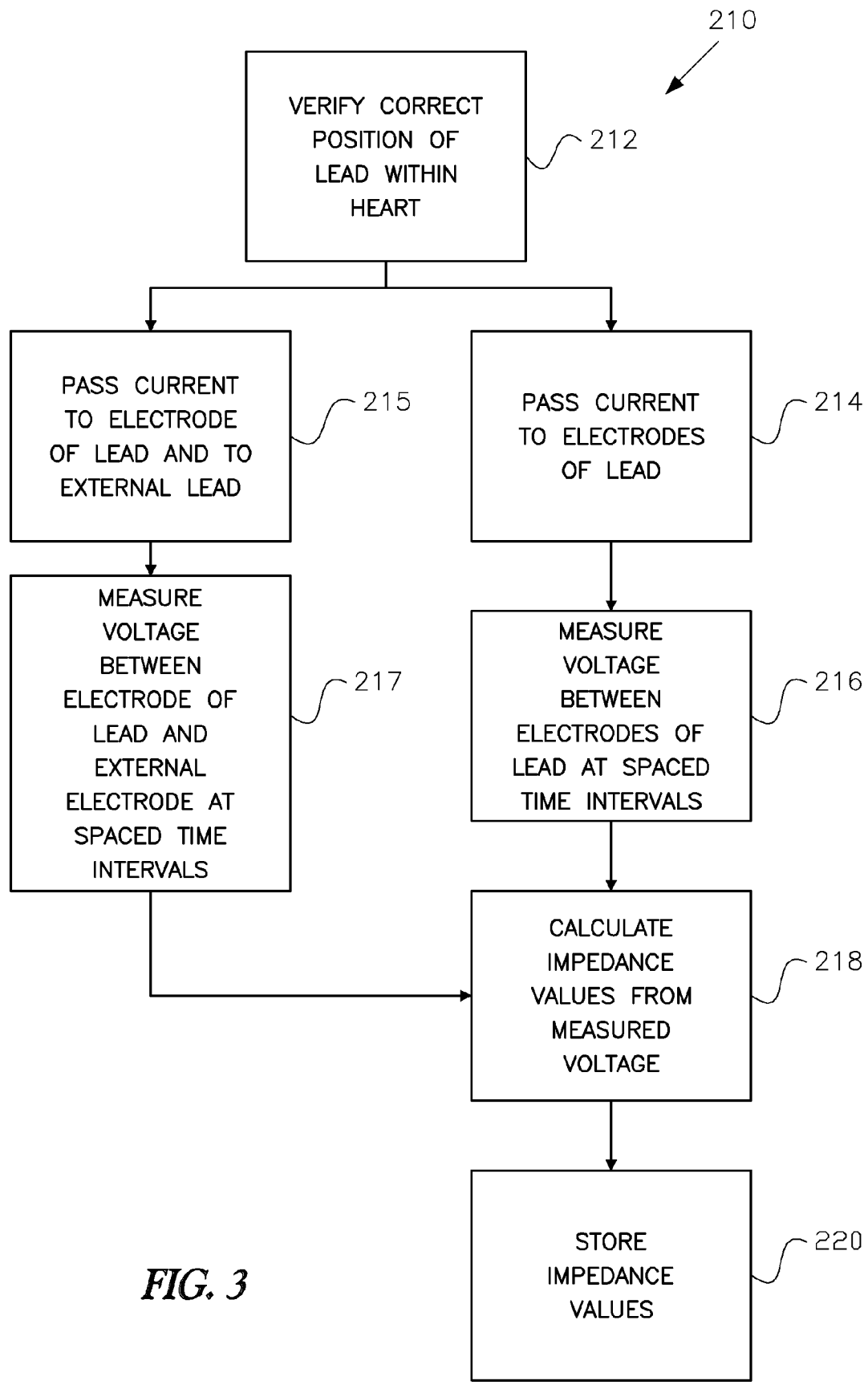
FIG. 3 is a schematic/block diagram illustrating generally, among other things, one embodiment of further portions of the measuring module of the impedance sensor of FIG. 2.
Figure 4:
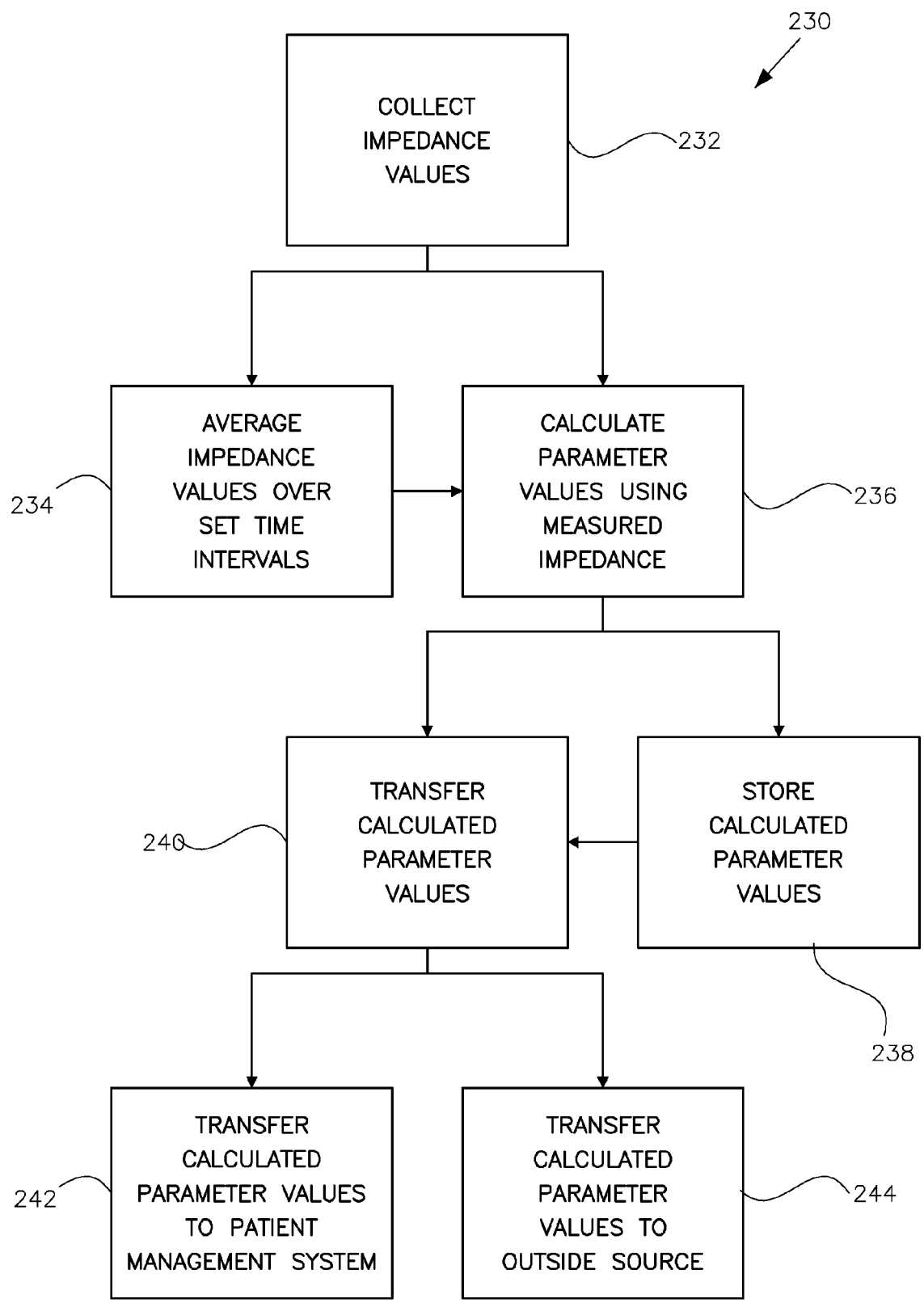
FIG. 4 is a schematic/block diagram illustrating generally, among other things, an embodiment of further portions of the parameter module of the impedance sensor of FIG. 2.

FIG. 3 illustrates several functions and capabilities of measuring module 210 as it relates to trending device 200 of the present invention. Measuring module 210 may be capable of performing such functions as verifying a correct position of a lead within heart 212, passing current between electrodes of the lead at spaced time intervals 214, measuring voltage between electrodes of the lead 216, calculating impedance values from the measured voltage 218, and storing impedance values 220.

Verifying the correct position of a lead within heart 212 may include verifying that the lead is correctly positioned within a heart chamber, such as chambers 116-122 of FIG. 1 (leads 126 and 128), or within a vessel of the heart, such as vessel 124 shown in FIG. 1 (leads 130 and 132). Verification of the correct position of the lead 212 may not be a required function for the measuring module as the position of the lead may be assumed to be correct when an operator of device 200 activates the device to begin measuring. In some cases, however, verification of that the lead is correctly positioned in the heart may be part of the sensing capabilities of measuring module 210.

Passing current to electrodes of the lead at spaced time intervals 214 may include passing current to one or more electrodes of a lead within the heart, or to an electrode positioned within the heart and to a separate electrode position external the heart (step 215 in FIG. 3), such as, for example, electrodes 134, 136 shown in FIG. 1. The current may be passed to the electrodes of the lead at a constant rate or at spaced time intervals. The frequency in which current is passed to electrodes of the lead may coincide with the voltage measurements being taken between the electrodes of the lead 216. The voltage measurements may also be taken between the lead electrode and the external electrode 217. Preferably, current is provided to the electrodes so that voltage measurements can be taken at any desired time or time interval. For example, voltage measurements could be taken only during what would typically be when the patient is sleeping, when the patient is exercising, or any number of combinations of time periods throughout a given day, week, etc.

The measured voltage is then used for calculating impedance values 218. The calculated impedance values may be sent directly to the parameter module 230 shown in FIG. 4, stored within device 200, or may be transferred to an outside source for storage. Storing impedance values 220 may include storing the impedance values into an array or a like format that reflects variables related to the voltage and impedance values.

The parameter module 230 may be capable of performing such functions as collecting impedance values 232, averaging impedance values over set time intervals 234, calculating parameter values using calculated impedance values 236, storing calculated parameter values 238, and transferring calculated parameter values 240 to, for example, an advanced patient management system 242 or to another outside source 244.

Collecting impedance values may include accessing the stored impedance values, for example, from a stored array of impedance values. The impedance values may be averaged over set time intervals prior to being used to calculate parameter values, or may be directly calculated into parameter values. Averaging impedance values over set time intervals 234 may include averaging the impedance values on, for example, a daily basis, a weekly basis, or other desired set time interval. The calculated parameter values may be stored within device 200 for future processing by device 200, or for future transfer of the parameter values to an outside source. Calculated parameter values may also be directly transferred to a patient management system or to an outside source that may, in other embodiments, perform the trending and analyzing functions of modules 250 and 270.

Figure 5:
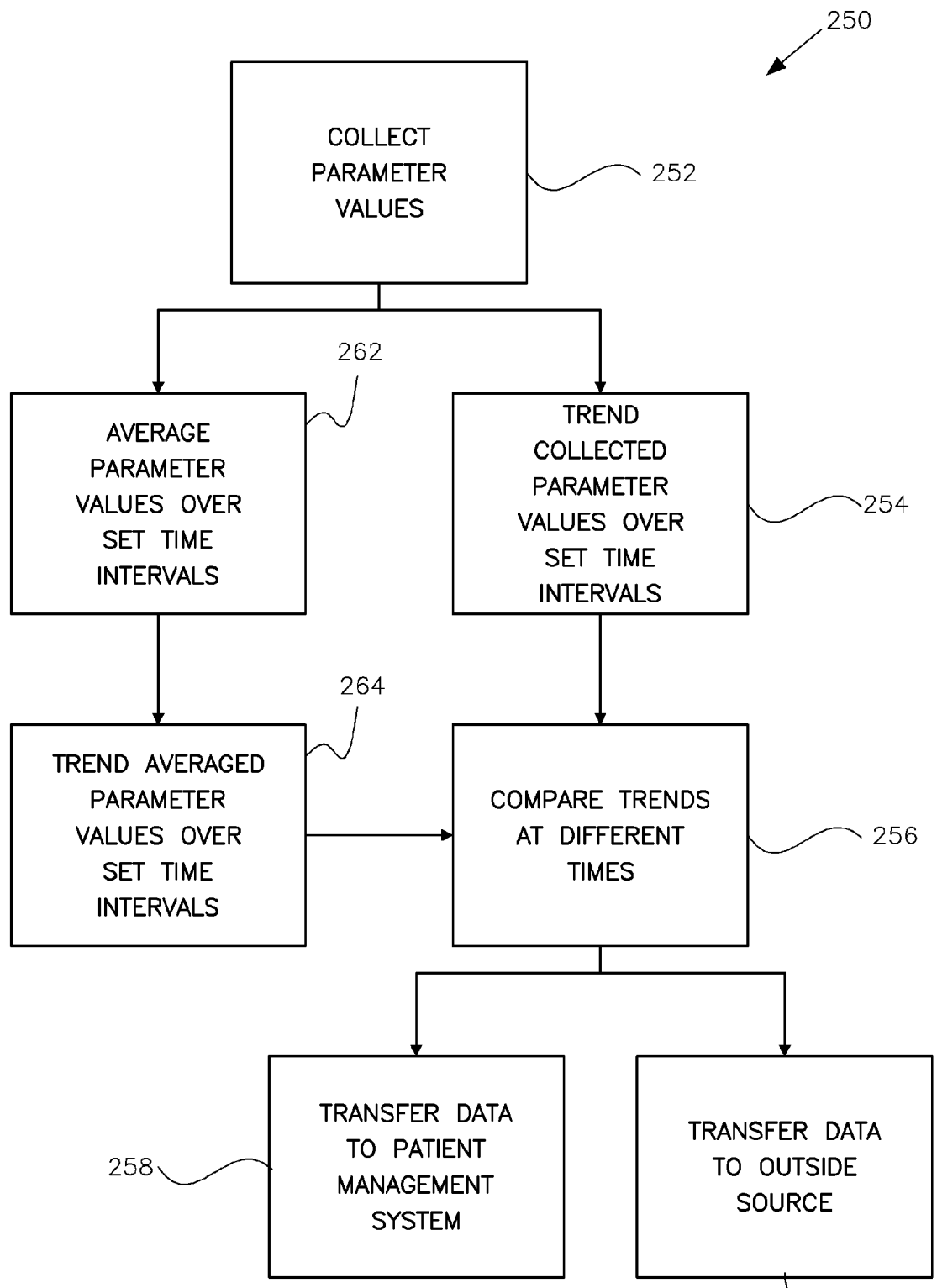
FIG. 5 is a schematic/block diagram illustrating generally, among other things, an embodiment of further portions of the trending module of the impedance sensor of FIG. 2.

The trending module 250, shown in FIG. 5, may be capable of performing several functions. For example, trending module 250 may collect parameter values 252, trend collected parameter values over set time intervals 254, compare trends at different times 256, transfer data to a patient management system 258, transfer data to an outside source 260, average parameter values over set time intervals 262, and trend average parameter values over set time intervals 264.

Collecting parameter values 252 may include collecting all parameter values stored by the parameter module 230, or collecting only certain parameter values at certain time intervals. Trending collected parameter values over a set time interval 254 may coincide with which parameter values are collected. Trending collected parameter values may include determining changes in parameter values over certain time intervals, such as, for example, changes in an average parameter value for each hour during a 24-hour period, for each day during a 7-day week, for each week during a given month, or for each month over the course of a year, etc. A "trend" may be generally defined as a pattern over a period of time, such as, for example, a net increase over time, a gradual, incremental increase over time, a steady value over time, etc. Comparing trends at different times 256 may not be required in all embodiments of trending module 250.

As stated above, averaging parameter values over set time intervals 256 may be used for trending over set time intervals 264. Thus, either specific parameter values or average parameter values may be compared to obtain trend data. Trend data may be transferred to an advanced patient management system 258 or to another outside source 260 that may be associated with device 200.

The trend data output by trending module 250 may be analyzed in several different ways. For example, trend data may be analyzed by analyzing module 270 that is part of device 200. In other embodiments, an individual, or some type of analyzing system or module, such as external analyzing module 156 in FIG. 1, that is independent of device 200, may perform analysis of trend data.

Figure 6:
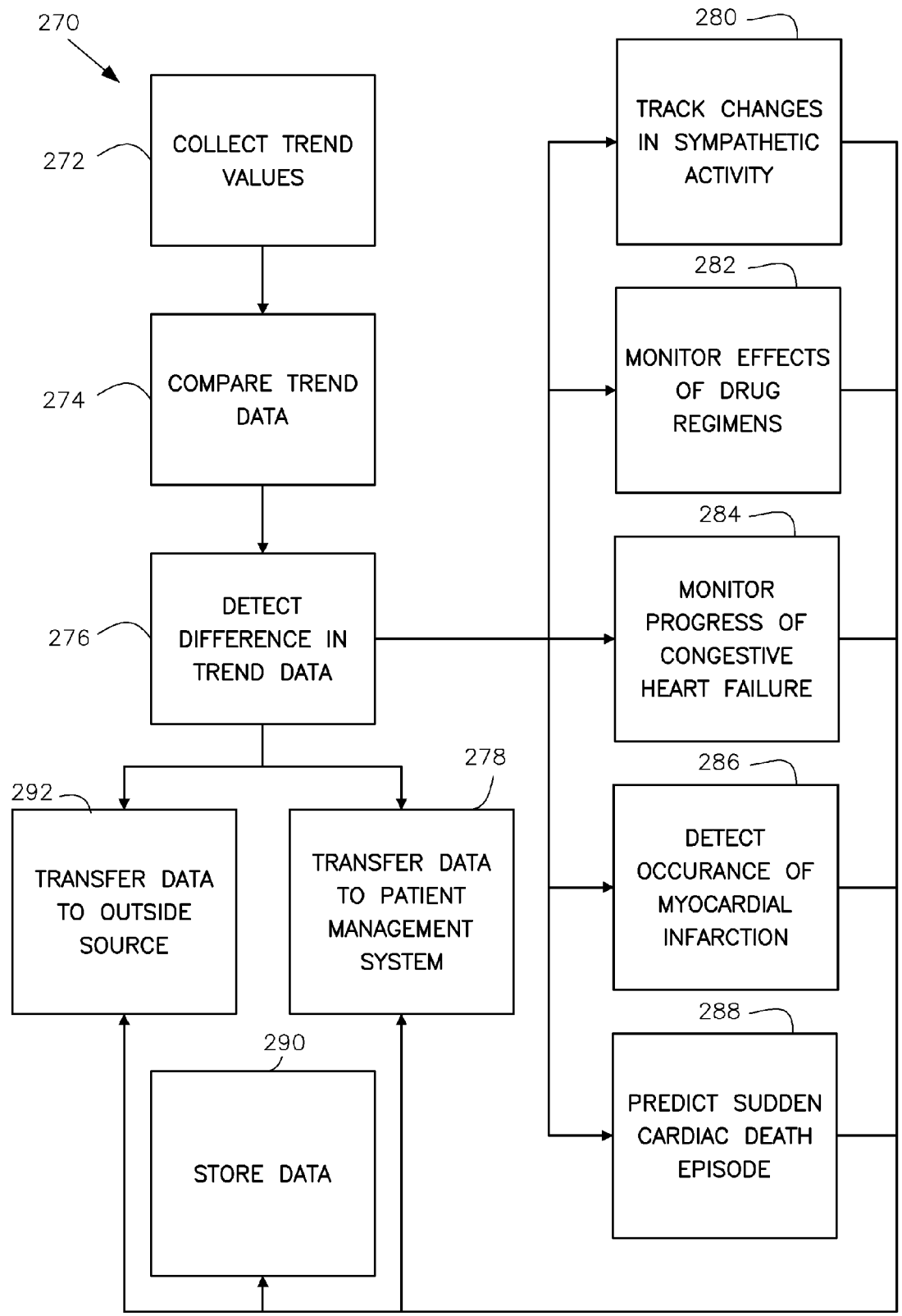
FIG. 6 is a schematic/block diagram illustrating generally, among other things, an embodiment of further portions of the analyzing module of the impedance sensor of FIG. 2.

Analyzing module 270 may be capable of performing several functions such as those shown in FIG. 6. For example, analyzing module 270 may collect trend data 272, compare trend data 274, detect differences in trend data 276, and transfer trend data to a patient management system 278. Analyzing module 270 may also track changes in sympathetic activity 280, monitor effects of drug regimens 282, monitor progress of congestive heart failure 284, detect occurrence of myocardial infarction 286, predict sudden cardiac death episode 288, store results 290, and transfer results to an outside source 292. The functions of collecting trend data 272, comparing trend data 274 and detecting differences in trend data 276 may involve further analysis and processing of trend information generated by trending module 250, the results of which may be transferred, for example, to an advanced patient management system 278 or another outside source 292. The trend data that is collected, compared, and detected may be used to track certain physiological indicators, such as indicators 280-288.

Trend data analyzed by analyzing module 270 may be generally used to track or monitor sympathetic activity (tone) 280. Changes in sympathetic activity, inferred from trend data may be useful diagnostic information for physicians. For example, the trend data may be used to monitor the effects of a drug or neural stimulation regimen being given a patient to alter sympathetic activity. The trend data may also be used to monitor the progress of congestive heart failure in a patient. Monitoring trend data related to intracardiac impedance could be used instead of R-R interval frequency spectrum (a conventional approach) or to augment such frequency-based sympathetic tone measurements.

Trend data may also be useful for detecting the occurrence of myocardial infarction 286. This type of detection is possible because a myocardial infarction typically triggers electrical remodeling which leads to increased cardiac sympathetic nerve density. Thus, detecting the occurrence of a myocardial infarction may be important because research has indicated that as many as one out of every three myocardial infarctions are considered to be unnoticed by the patient. In addition, myocardial infarction is usually an eventual precursor to sudden cardiac death episode (SCD).

A further use of trend data may be in predicting SCD. Changes in sympathetic activity, as may be inferred from certain types of trends in such physiological parameters as described above, may indicate the onset of an SCD.

Early recognition by a patient or the patient's physician of increases of sympathetic activity over time (as indicated by trend data) may provide an opportunity for earlier treatment for the patient.

In some embodiments, the analyzing module of system 200 may be able to store results within device 200 for future transmission to an outside source, or may immediately transfer results to an advanced patient management system. Some advanced patient management systems may include an alarm or similar indicator that would alert the patient or the patient's physician if, for example, a certain threshold value is met. Other patient management systems may be configured to connect to a communications system, such as, for example, a telecommunications system, the Internet via a hard landline or wireless network system, or satellite system to automatically send patient data at spaced time intervals or continuously send data in real time.

Figure 7:
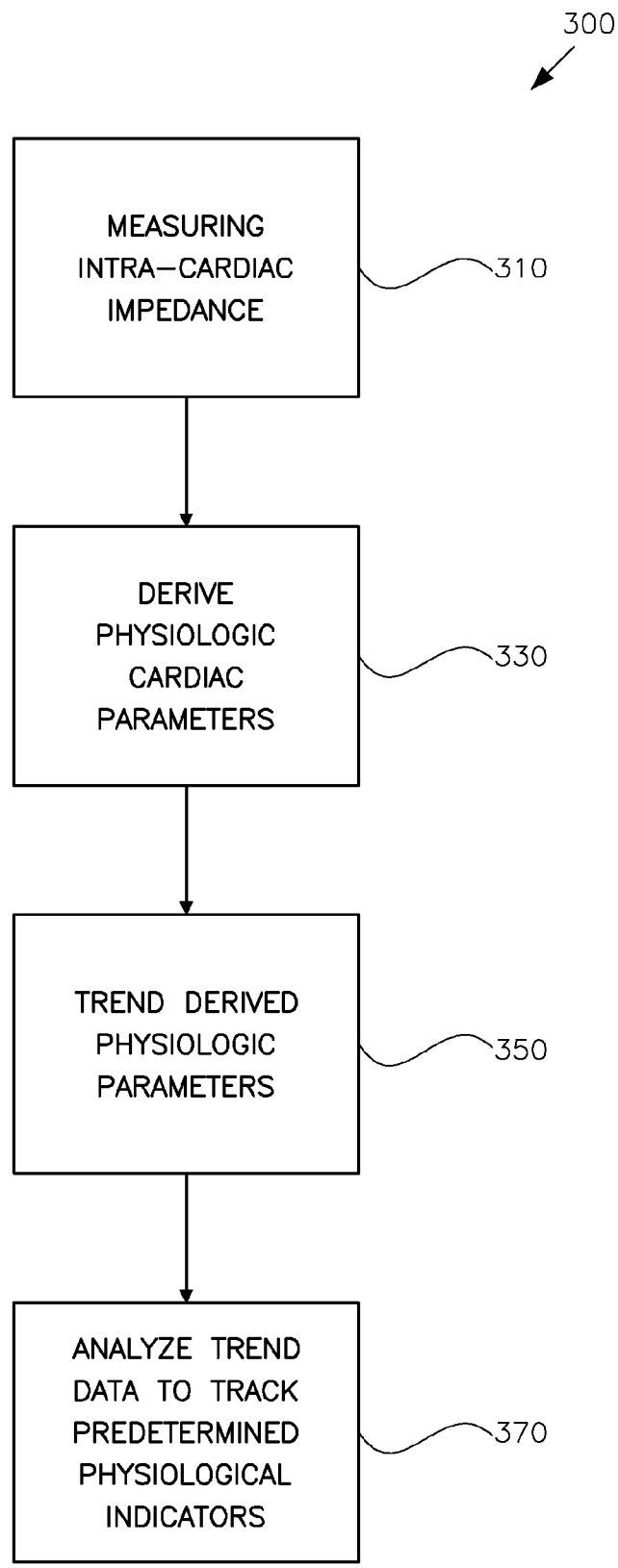
FIG. 7 is a schematic/block diagram illustrating generally, among other things, another embodiment of portions of the impedance sensor.

One example of a method of trending physiologic parameters is shown in FIG. 7. Method 300 may include the steps of measuring intracardiac impedance 310, deriving physiologic cardiac parameters 330, trending derived physiological parameters 350, and analyzing trend data to track predetermined physiological indicators 370. Each of steps 310, 330, 350 and 370 may include steps or functions that coincide with those functions described with reference to modules 210, 230, 250 and 270, respectively, and to systems 100 and 200 generally.

The functions performed by the system and method discussed above may be performed by a single unitary device, such as an implantable cardiac rhythm management device. The instructions for performing the steps of the method and the functions related to the device discussed above may be stored on a computer readable medium having computer executable instructions. The present invention may also include a computer data signal embodied in a carrier wave readable by a computing system and encoding a computer program of instructions for executing a computer program of instructions for executing a computer program performing the method steps and system functions discussed above.

In some instances, various cardiac rhythm management (CRM) devices that are currently sold and marketed may be modified in order to practice the present invention. For example, if a given CRM device includes hardware capable of performing necessary intracardiac impedance measurements, the software of the system may be modified or augmented for software that performs the impedance measuring, parameter deriving, trending and analyzing functions required by the present invention.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the fill scope of equivalents to which such claims are entitled. In the appended claims, the terms "including" and "in which" are used as the plain-English equivalents of the respective terms "comprising" and "wherein."

I claim:

1. A system for monitoring congestive heart failure, the system comprising:
   a measuring device configured to measure, using a lead, intra-cardiac impedance of a patient when the patient is typically sleeping;
   a derivation module configured to:
      derive a physiologic cardiac parameter from the measured impedance, the derived parameter including at least one of stroke volume, ejection fraction, and pre-ejection period; and
      derive sympathetic activity from the physiologic cardiac parameter;
   a trending module configured to trend the derived sympathetic activity over spaced time intervals to create trended sympathetic activity data; and
   an analyzing module configured to analyze the trended sympathetic activity data to monitor congestive heart failure status from the analysis.

2. The system of claim 1, wherein the analyzing module is configured to:
   compare the trended sympathetic activity data; and
   detect a difference between the trended sympathetic activity data.

3. The system of claim 1, comprising a reporting module configured to report the trended sympathetic activity data to an outside source.

4. The system of claim 1, wherein the derivation module and the trending module are packaged with an implantable device.

5. The system of claim 1, comprising an external device configured to store the trended sympathetic activity data.

6. The system of claim 1, comprising a separately located device, wherein the system is configured to download the trended sympathetic activity data to the separately located device.

7. The system of claim 6, wherein the separately located device includes an external patient management system.

8. The system of claim 1, wherein the measuring device is configured to measure intra-cardiac impedance using an implantable cardiac rhythm management device.

9. The system of claim 1, wherein the measuring device is coupled to at least two electrodes configured to measure a voltage resulting from a current applied between the at least two electrodes, wherein the voltage is used to determine the intra-cardiac impedance.

10. A device for trending sympathetic activity, the device comprising:
    an impedance module configured to measure, using a lead, an intra-cardiac impedance of a patient at spaced time intervals when the patient is typically sleeping;
    a derivation module configured to:
       derive a physiologic cardiac parameter from the measured impedance, the derived parameter including at least one of stroke volume, ejection fraction, and pre-ejection period; and
       derive the sympathetic activity using the physiologic cardiac parameter;
    a trending module configured to generate trended sympathetic activity data using the derived sympathetic activity; and
    an analyzing module configured to analyze the trended sympathetic activity data to monitor congestive heart failure status from the analysis.

11. The device of claim 10, comprising a reporting module configured to report the trended sympathetic activity data to an outside source.

12. The device of claim 10, wherein the impedance module is in communication with at least two electrodes, the at least two electrodes being configured to measure a voltage resulting from a current applied between the at least two electrodes, wherein the voltage is used to determine the intra-cardiac impedance.

13. The device of claim 10, wherein the device is configured to download the trended sympathetic activity data to an external storage device.

14. A device-readable medium comprising instructions that, when performed by a previously-implanted medical device, cause the device to perform acts comprising:
    measuring, using a lead, an intra-cardiac impedance of a patient at spaced time intervals when the patient is typically sleeping;
    deriving a physiologic cardiac parameter from the measured impedance, the derived parameter including at least one of stroke volume, ejection fraction, and pre-ejection period;
    deriving sympathetic activity using the physiologic cardiac parameter;
    generating trended sympathetic activity data using the derived sympathetic activity;
    analyzing the trended sympathetic activity data; and
    monitoring congestive heart failure status from the analysis.

15. The device-readable medium of claim 14, wherein analyzing the trended sympathetic activity data includes:
    comparing the trended sympathetic activity data; and
    detecting a difference between the trended sympathetic activity data.

16. The device-readable medium of claim 14, comprising instructions that, when performed by the previously-implanted medical device, cause the device to perform acts comprising reporting the trended sympathetic activity data to an outside source.

17. The device-readable medium of claim 14, comprising instructions that, when performed by the previously-implanted medical device, cause the device to perform acts comprising storing the trended sympathetic activity data on an external device.

* * * * *